United States Patent [19]
Niznick et al.

[11] Patent Number: 5,433,606
[45] Date of Patent: * Jul. 18, 1995

[54] INTERLOCKING, MULTI-PART ENDOSSEOUS DENTAL IMPLANT SYSTEMS

[75] Inventors: Gerald A. Niznick, Las Vegas, Nev.; Alan R. Balfour, Camarillo, Calif.

[73] Assignee: Core-Vent Corporation, Las Vegas, Nev.

[ * ] Notice: The portion of the term of this patent subsequent to Aug. 2, 2011 has been disclaimed.

[21] Appl. No.: 99,070

[22] Filed: Jul. 28, 1993

[51] Int. Cl.$^6$ .............................................. A61C 8/00
[52] U.S. Cl. ................................................... 433/173
[58] Field of Search ............... 433/172, 173, 174, 175, 433/176

[56] References Cited

U.S. PATENT DOCUMENTS

| | | | |
|---|---|---|---|
| 4,492,577 | 1/1985 | Farris et al. | 433/173 |
| 4,547,157 | 10/1985 | Driskell | 433/173 |
| 4,645,453 | 2/1987 | Niznick | 433/173 |
| 4,713,003 | 12/1987 | Symington et al. | 433/173 |
| 4,713,004 | 12/1987 | Linkow et al. | 433/174 |
| 4,854,872 | 8/1989 | Detsch | 433/173 |
| 4,955,811 | 9/1990 | Lazzara et al. | 433/173 |
| 4,960,381 | 10/1990 | Niznick | 433/174 |
| 5,145,371 | 9/1992 | Jorneus | 433/173 |
| 5,169,309 | 12/1992 | Staubli et al. | 433/173 |
| 5,213,502 | 5/1993 | Daftary | 433/172 |

FOREIGN PATENT DOCUMENTS

| | | | |
|---|---|---|---|
| 0288444 | 10/1988 | European Pat. Off. | 433/173 |
| 2635455 | 2/1990 | France | 433/174 |
| 2199502 | 7/1988 | United Kingdom | 433/174 |

OTHER PUBLICATIONS

"Rotational Accuracy of Implant Components for Single-Tooth, Root-Implants," Dental Implantology Update, vol. 2, No. 1, Jan. 1991.
Swede-Vent Prosthetics-A Breakthrough for Branemak Implant Users, Core-Vent, Feb. 1, 1994.

*Primary Examiner*—Nicholas D. Lucchesi

[57] ABSTRACT

An endosseous dental implant system includes a dental implant having a multi-sided projection at its top end and an internally threaded or unthreaded passage extending into the body of the implant through an opening in the projection at the top of the implant, and an abutment having an internal passage for receiving a fastener that passes through the internal passage of the abutment, and threads into the internal passage inside the implant. The abutment has a multi-sided internal cavity at its bottom end with each of the cavity sides perpendicular to the longitudinal axis of the abutment so that the cavity, when seated over the projection at the top of the implant, forms an anti-rotational, interlocking junction with the implant.

20 Claims, 5 Drawing Sheets

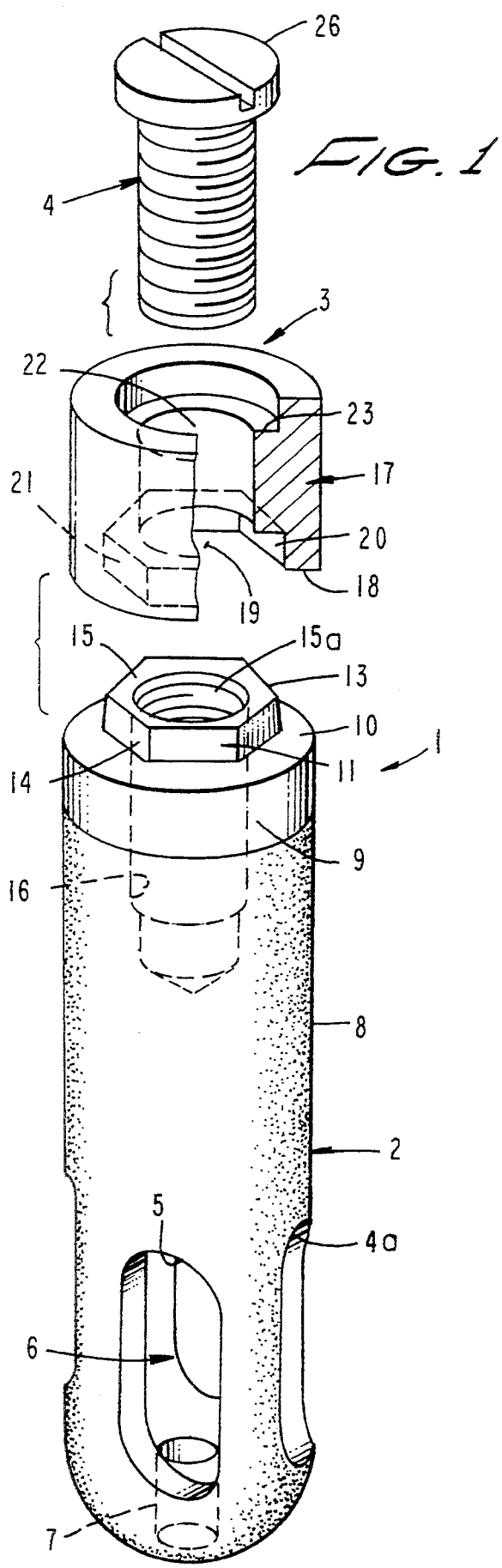
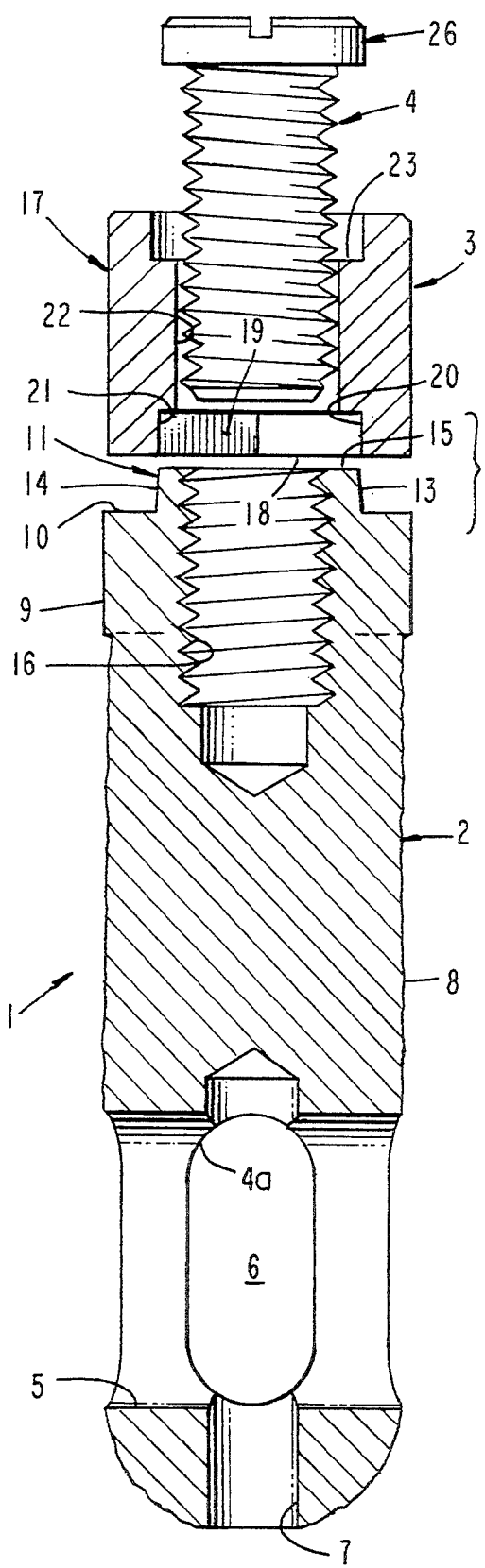
FIG. 1
FIG. 2

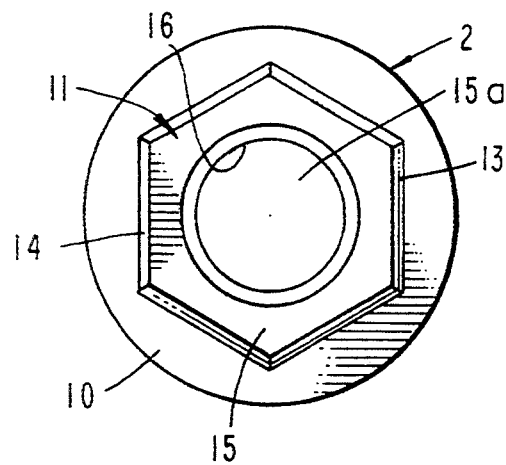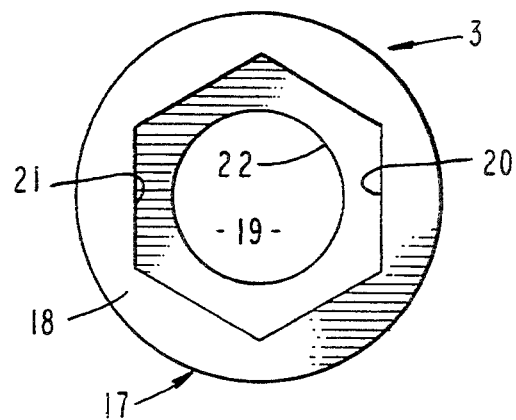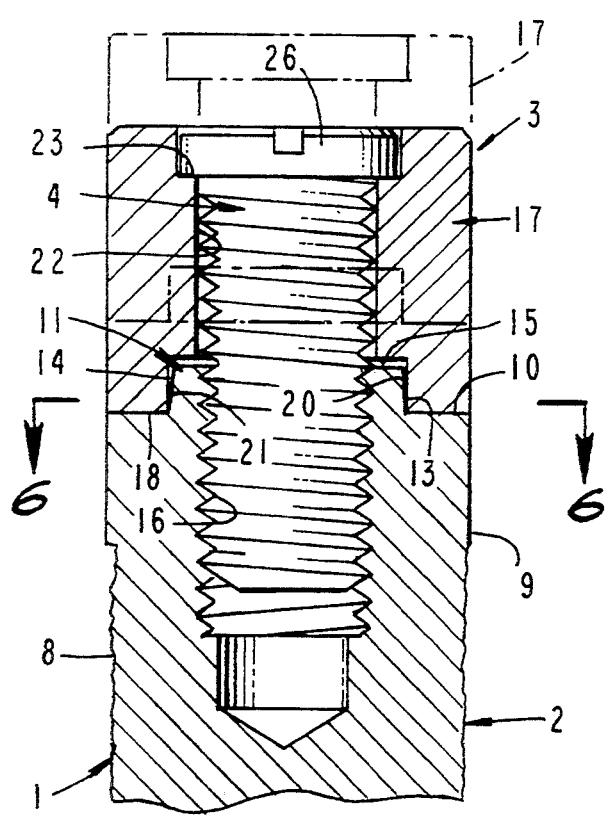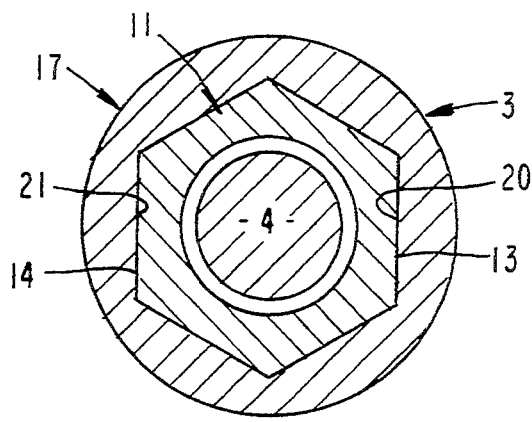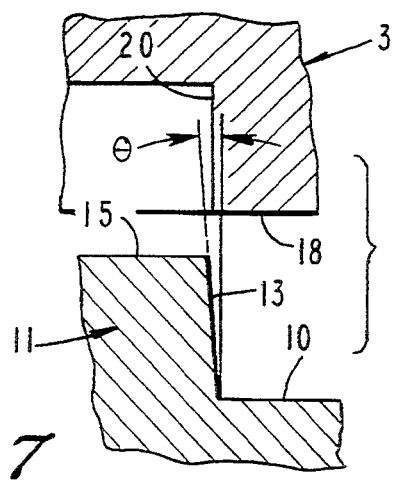

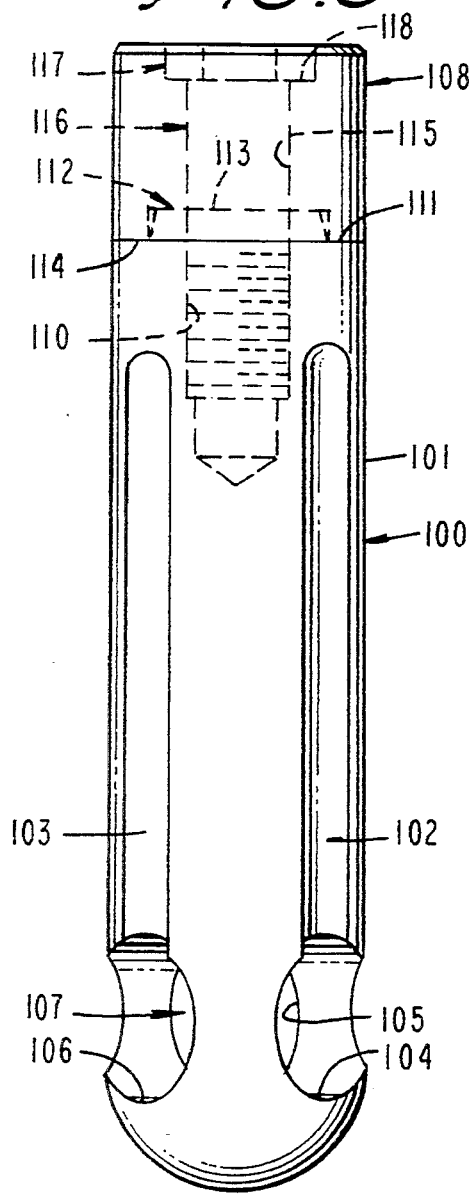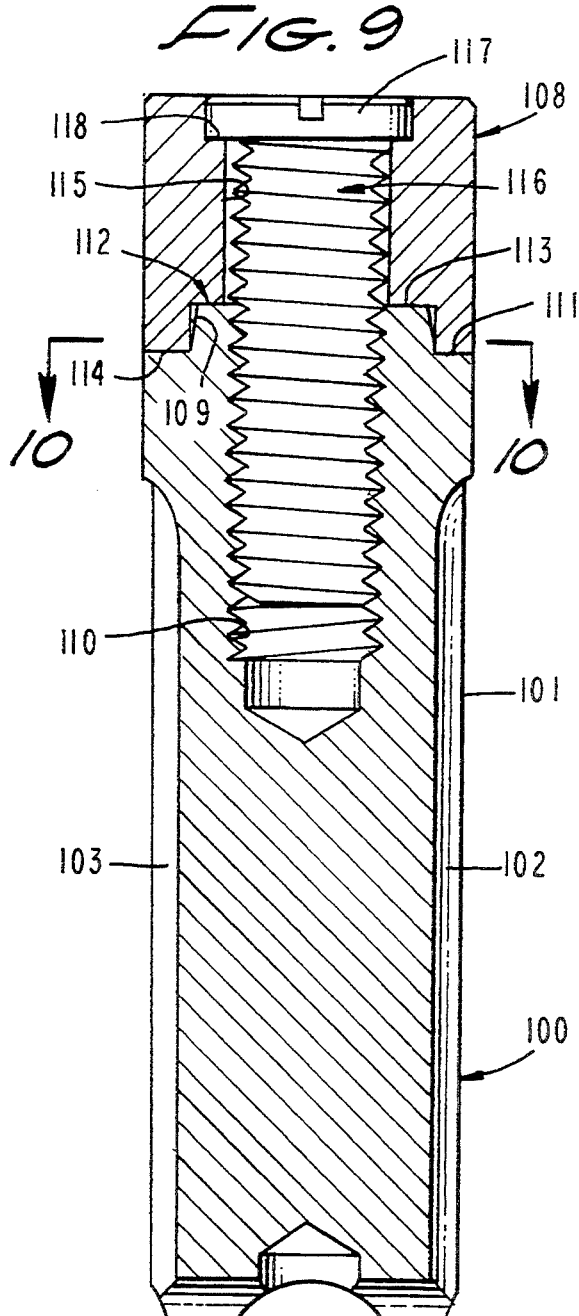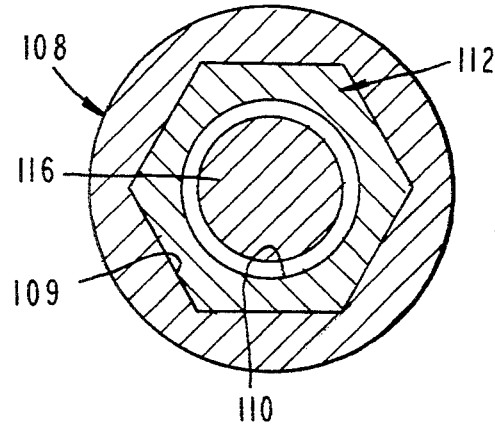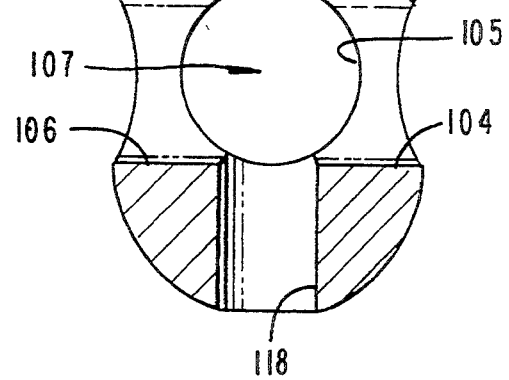

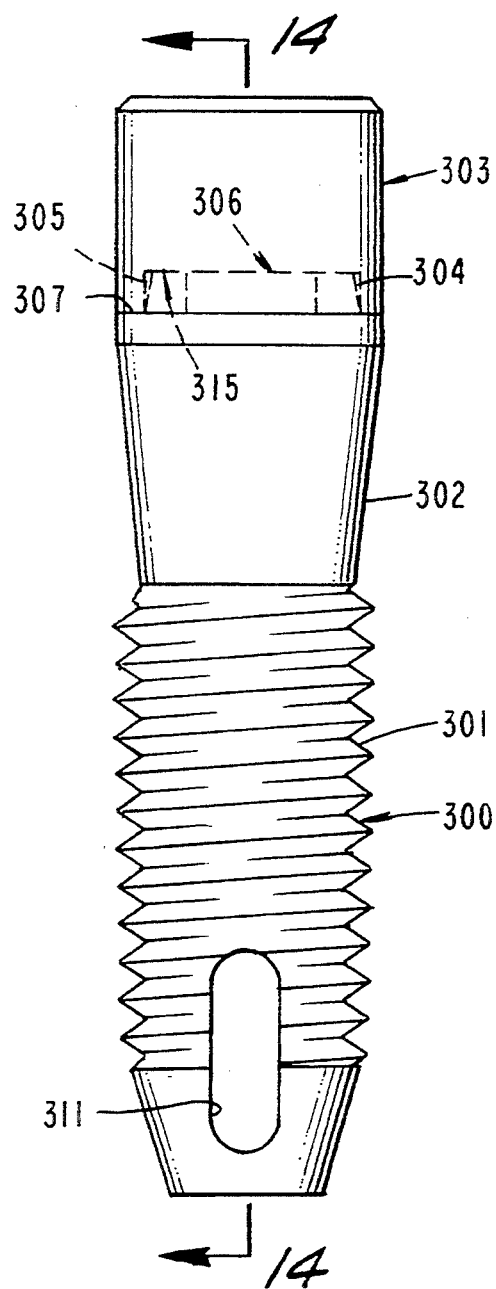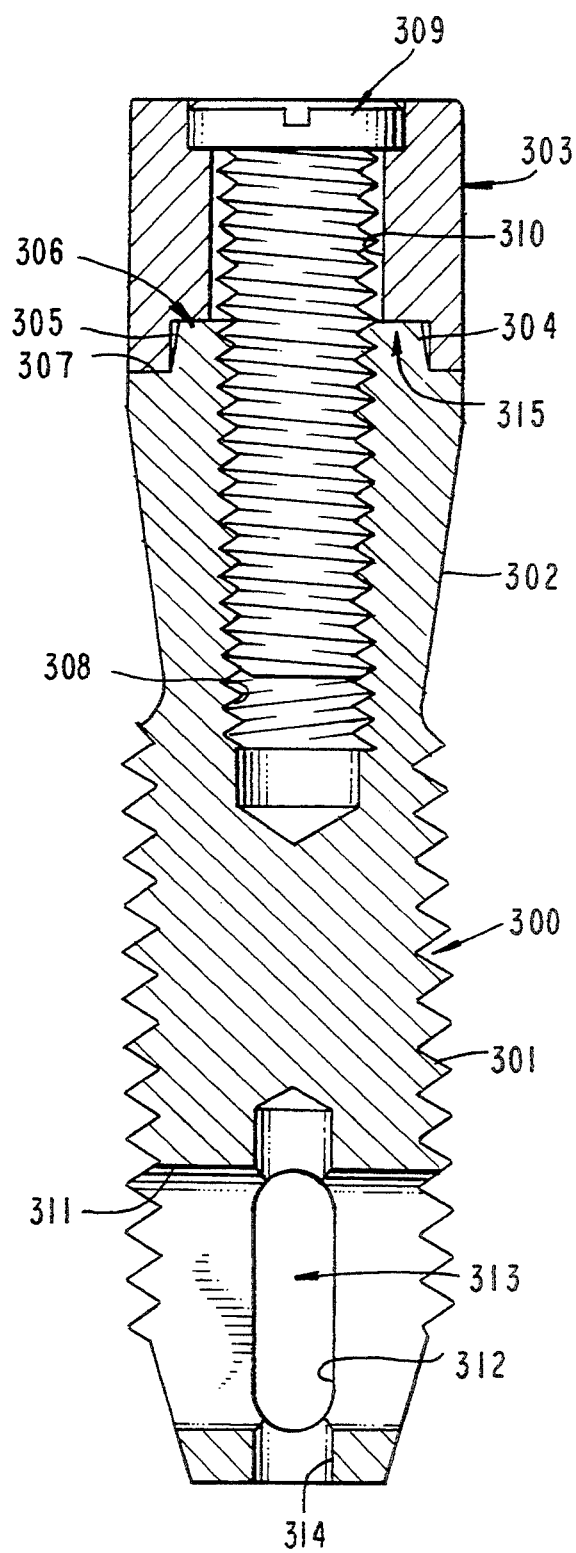

INTERLOCKING, MULTI-PART ENDOSSEOUS DENTAL IMPLANT SYSTEMS

FIELD OF THE INVENTION

This invention relates to an endosseous dental implant system that includes at least two parts: a first part called a dental implant, and a second part called an abutment, post or insert. Such dental implants may have a threaded external sidewall surface or a non-threaded external sidewall surface, and the implants themselves may be generally cylindrical in shape. Near one end of such implants there may be one or more cross-vents through the sidewall of the implant, and, sometimes, an apical hole near the bottom end of the implant, preferably connected to the cross-vents.

The external sidewall surface may also have one or more longitudinally extending grooves, and may include a coating such as hydroxyl apatite over all or part of the external sidewall surface. At the other end of such implants is a projection, preferably a multi-sided projection, for engaging, and interlocking, anti-rotationally, with a cavity inside an opening in the second part of the implant system. One or more of these sides tapers downwardly and outwardly, preferably from an upper, substantially flat surface, to a lower surface, forming locking surfaces that engage and lock with corresponding, substantially perpendicular wall surfaces of the cavity inside the second part of the dental implant system.

BACKGROUND OF THE INVENTION

Two-part endosseous dental implant systems for insertion in a wholly or partially edentulous region of the jawbone of a patient have been in use for a few years. These implant systems may be completely embedded in the jawbone, covered with mucosal tissue, and permitted to remain in place while new bone grows around the implant, and into and/or through one or more vent holes in the implant itself. Once the implant has become firmly anchored in bone, the mucosal tissue is reopened, and an abutment or post is connected to the implant using a screw. A prosthesis can then be connected to the abutment or post.

Many of these two-part implant systems have, at the top end of the implant, an external, hexagonal projection, sometimes called a male hex, which projects upwardly from the top end of the implant, leaving a shoulder surrounding the base of the male hex. An abutment or post having an outer diameter that substantially matches the outer diameter of the implant is seated on the male hex to form a substantially sealed connection. Some of these implants have an externally-threaded, sidewall portion which can be screwed into an opening formed in bone after bone tissue has been removed from the jawbone, as depicted, for example, in U. K. Patent No. 1,291,470 or in U.S. Pat. No. 4,713,004. With implant systems of this kind, the male hex projection at the top of the implant is used to insert the implant in the jawbone, using an inserting device, e.g. a wrench, which is attached to the male hex.

Another kind of two-part, endosseous dental implant system with an external male hex is a cylindrical implant with a non-threaded, external body portion. These implants are pushed into an opening formed in bone tissue. An example of this type of implant is Core-Vent Corporation's BIO-VENT implant.

In implants of these kinds with external male heads, the male head is used to attach the implant to an abutment or post having a matching female, hex-shaped cavity that receives and engages the male hex projection. Such male hex heads and female hex cavities are sometimes referred to as coupling surfaces. The implant systems that now have such external hexes for coupling with an internal hex cavity on an abutment have the walls of the hexagonal head of the implant and the hex-shaped cavity of the abutment perpendicular and parallel to one another.

With such implant systems, the male hex of the implant is smaller in diameter than the diameter of the hex-shaped cavity of the abutment to permit the male hex to fit inside the female cavity. This difference in diameter is sufficiently large to allow for manufacturing variations while still allowing the coupling surfaces of the abutment to seat fully on the shoulder of the implant to create a sealed outer margin between abutment and implant. However, this leaves space between the coupling surfaces of the male and female hexes.

Within the hex head region, and extending into the implant itself, there is in such implants a threaded hole for receiving an attachment screw of a mating abutment. The abutment typically has an interior passage centered on its hex cavity. When attaching the abutment to the implant, the screw is inserted through the abutment passage and is screwed into the threaded implant hole. Tightening the screw also tightens the abutment against the implant. When the screw is tightened until the external hex of the implant mates with the matching female hex cavity in the abutment, the system is secured against axial displacement of the abutment from the implant.

According to reported studies, the seating of the external hex of the implant within the female hex cavity of the abutment, where both the external hex and the internal hex cavity have parallel walls, results in the full seating of the abutment onto the shoulder surrounding the external male hex of the implant, but fails to prevent rotational displacement of the implant with respect to the abutment.

One scientific study presented by Dr. Paul Binon at the Academy of Osseointegration meeting in San Diego, Calif. in March, 1993, documented that the coupling surfaces of commercially-available implants of these kinds have four to five degrees of rotation between them. Dr. Binon later reported that the Branemark implant/abutment assembly of this kind exhibits up to nine degrees of rotation between the implant and the abutment. The attachment between abutment and implant formed in this way is unstable. Lateral forces from biting are transmitted to the screw joining the abutment to the implant rather than the coupling surfaces of the external hex projection on the implant and the internal hex cavity in the abutment. As a result, the screw that joins the implant to the abutment may break or loosen. Rotational instability may also adversely affect the accuracy of transfer procedures needed for the indirect fabrication of a final prosthetic restoration on such implant/abutment assemblies.

U.S. Pat. No. 4,547,157 discloses an implant having a conical projection for mating with an abutment having a matching cavity. A small degree of taper of the two surfaces results in a friction fit between the parts that tends to maintain the connection. These systems do not use a screw that passes through the abutment to lock the abutment to the implant. In this implant/abutment connection system, no shoulder exists on the head of the implant for the outer edge of the walls of the internal cavity to rest upon and seal. With this tapered, cylindrical coupling surface making direct contact on full seating of the abutment in the implant, a good connection results. However, this type of connection results in a ledge being formed as the outer walls of the internal cavity fit over the conical projection of the implant. This ledge can trap food particles and irritate the gum tissue. Moreover, because the projection and mating cavity are conical, they provide little resistance to rotational forces that tend to loosen the connection.

SUMMARY OF THE INVENTION

This invention relates to a multi-part, endosseous dental implant system having inter-locking, anti-rotational surfaces on the two parts of the system called the dental implant and the abutment. One part of the system, called the implant, has a generally-cylindrical shape, preferably (but not necessarily) tapering at the bottom to a region that preferably includes one or more cross-vents formed in the sidewall of the implant. Preferably, at the bottom end, the implant has an apical hole that extends upwardly into the body of the implant, preferably connecting with the openings formed by the cross-vents. The external sidewall of the implant may include a plurality of screw threads, either self-tapping or non-self-tapping, of a substantially constant pitch. These threads may extend along the entire external sidewall surface, or along only part of the external sidewall surface. Above the threaded portions, if any, of the external sidewall surfaces, the sidewall of the implant body may be substantially cylindrical, or may taper upwardly and outwardly or upwardly and inwardly toward the top end. At the bottom end, the sidewall of the implant may be substantially cylindrical, or may taper toward the bottom, and may be threaded substantially entirely, or just partially, toward the bottom end.

At the top end of these implants there is a male projection, preferably multi-sided, preferably with a substantially flat upper surface, and preferably with an outer diameter that is smaller than the outer diameter of the implant itself. In preferred embodiments, this male projection at the top end of the implant has a plurality of sides, preferably four, six or more, that taper downwardly and outwardly toward a surface, preferably a substantially flat upper surface at the top end of the implant itself.

In preferred embodiments, the male projection, at its upper end, is sufficiently small to fit inside an internal, multi-sided female cavity located at the bottom end of the second part of this system which is called the abutment or post. The tapered sides of the male projection preferably taper downwardly and outwardly sufficiently to permit the male projection to enter the cavity without engaging the leading edges of the multi-sided cavity, then to engage frictionally these edges and the sides of this cavity. As the male projection enters the cavity more fully, the tapered walls of the male projection engage these edges and the sides of the cavity with increasing force as the cavity in the abutment is more fully seated over the male projection. When the cavity is fully seated on the male projection, the margin between the bottom end of the abutment and the top end of the implant is completely closed.

Preferably, the degree of taper from the top of the projection to the substantially flat upper surface at the top end of the implant is in the range of about one to about three degrees, and more preferably from about one to about one and one-half degrees. In preferred embodiments, all the sides of the multi-sided male projection at the top of the implant taper downwardly and outwardly from the upper surface of the projection to the upper surface of the implant itself. Not all of these sides must be tapered, however, provided at least one side, and preferably two opposing sides, are tapered.

The second part of the dental implant system, called the abutment or post, has at its bottom end an internal, multi-sided female cavity, with the same number of sides as the male projection at the top of the implant. This internal cavity extends upwardly into the abutment, and extends a distance that is, at a minimum, substantially equal to the height of the male projection. In that way, the abutment cavity can be fully seated upon the implant. The opposing sides of the cavity are substantially parallel to one another, and all sides of the cavity are substantially perpendicular to a plane perpendicular to the longitudinal axis of the abutment itself. The abutment is also preferably generally cylindrical in shape, and preferably has an outer diameter at the bottom end of the abutment that is substantially the same as the outer diameter of the top end of the implant. The abutment has a substantially flat bottom surface into which the female cavity projects, and that flat surface is adapted to seat upon and seal with the upper surface of the implant that surrounds the projection at the top end of the implant.

The abutment preferably includes an internal, preferably cylindrical passage for receiving a screw or other fastener that passes through the abutment, and screws into an internally-threaded passage in the implant for receiving the screw or other fastener. This internally-threaded passage in the implant preferably extends downwardly into the body of the implant from its top end, and is substantially centered on the male projection at the top end of the implant. Near the top of this internal, preferably cylindrical, passage inside the abutment is a flange surface for engaging the head of the screw or other fastener. Tightening of such a screw or fastener, in preferred embodiments, seats the abutment substantially fully upon the implant.

BRIEF DESCRIPTION OF THE DRAWINGS

This invention can better be understood by reference to the drawings, in which:

FIGS. 1 and 2 show a perspective view and an elevation view in cross-section, respectively, of a first embodiment of the dental implant systems in which an externally-unthreaded, endosseous implant has, at its top end, a substantially cylindrical-shaped, six-sided male projection with all six sides tapering downwardly and outwardly from a substantially flat upper surface to the top of the implant, and an abutment that has, at its bottom end, a six-sided female cavity to fit over, and interlock with, the tapered male hex at the top of the implant;

FIGS. 3 and 4 show a top plan view and bottom plan view, respectively, of the male hex projection with tapering sides at the top end of the implant shown in FIGS. 1 and 2, and inside the bottom end of the female cavity with untapered walls formed inside the abutment shown in FIGS. 1 and 2;

FIG. 5 shows the embodiment illustrated in FIGS. 1 and 2 with the abutment firmly seated atop the implant and the fastener passing through the passage inside the abutment and into the internally-threaded passage inside the implant;

FIG. 6 shows a top plan view, taken in cross-section on line 6—6 of FIG. 5, of the implant/abutment assembly shown in FIG. 5;

FIG. 7 shows, in exploded view, one of the tapered sidewalls of the projection at the top end of the implant shown in FIGS. 1 through 6 and the corresponding, interlocking, perpendicular wall of the internal cavity in the abutment also shown in FIGS. 1 through 6;

FIGS. 8, 9 and 10 show a second embodiment of an endosseous implant/abutment combination in which a six-sided male projection at the top end of the implant has six tapered sidewalls to interlock with the perpendicular sidewalls inside the cavity at the bottom of the abutment; FIG. 8 shows a side elevation view of the implant with an externally-unthreaded, longitudinally-grooved sidewall; FIG. 9 shows an elevation view in cross-section of this implant/abutment assembly; and FIG. 10 shows a top plan view of this assembly taken in cross-section on line 10—10 of FIG. 9;

FIG. 11 shows a side elevation view of the assembly, and FIG. 12 shows a side elevation view in cross-section taken on line 12—12 of FIG. 11; and FIGS. 13 and 14 show a fourth embodiment of an implant/abutment assembly, in which the implant has an externally-threaded sidewall, and a male projection with six downwardly-tapered sides at the top end of the implant, and the abutment has a corresponding female cavity at the bottom end with each of the six sides perpendicular, and with opposing sides in the cavity parallel to one another; FIG. 13 shows a side elevation view of the assembly, and FIG. 14, a side elevation view of this assembly in cross-section taken on line 14—14 of FIG. 13.

DETAILED DESCRIPTION OF THE PREFERRED EMBODIMENTS

Figure 11:
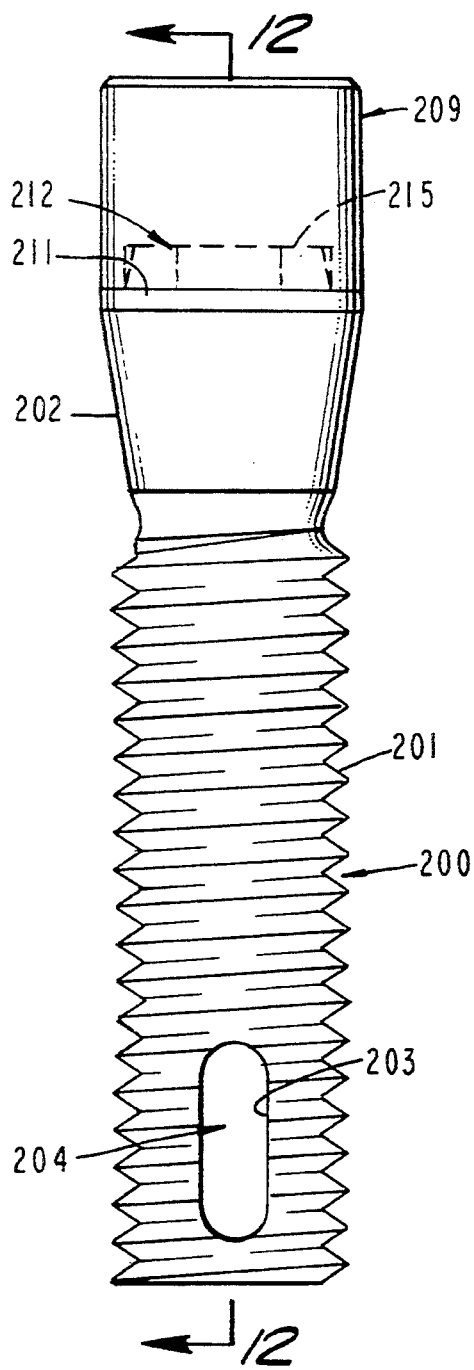
FIGS. 11 and 12 show a third embodiment of an implant/abutment assembly, in which the implant has an externally-threaded sidewall, and a male projection with six downwardly-tapered sides at the top end of the implant, and the abutment has a corresponding female cavity at its bottom end with each of the six sides perpendicular, and with opposing sides in the cavity parallel to one another.

FIG. 1 shows a two-part endosseous implant system 1 including generally cylindrical-shaped dental implant abutment 3, and cylindrical-shaped, threaded fastener 4. Dental implant 2 has a generally-cylindrical shape, unthreaded external sidewall 8, and a plurality of oval-shaped cross-vents such as cross-vents 4 and 5 that form an internal opening 6 inside implant 2. At the bottom of implant 2 is apical passage 7, which extends upwardly into implant 2, and connects to internal opening 6. Unthreaded external sidewall 8 of implant 2 has a toughened surface formed, for example, by a plasma spray or coating. Near the top end of implant sidewall 8 is cylindrical, smooth-surfaced sidewall region 9. Above sidewall region 9, at the top end of implant 2, is six-sided male projection substantially centered on flat upper surface 10, which surrounds projection 11.

Projection 11 has six sides, such as sides 13 and 14. Each of these sides tapers downwardly and outwardly from substantially flat upper surface 15 of projection 12, to surface 10, preferably at an angle with respect to the longitudinal axis of implant 2, of about one and one-half degrees. Projection 11 has a center opening 16 which extends downwardly into a passage 16 inside implant Passage 16 is threaded along at least a portion of its interior surface for engagement with threaded fastener 4.

Abutment 17 has a generally cylindrical, unthreaded outer wall surface, and has, at its bottom end, substantially the same outer diameter as the outer diameter of region 9. Abutment 17 also has, at its bottom end, a flat, lower surface 18 surrounding internal, female cavity 19. Cavity 19 has six inner sides 20 and 21, all substantially perpendicular to surface 19, and all substantially untapered. Opposing sides inside cavity are parallel to one another. Inside abutment 17 is cylindrical-shaped through passage 22. Passage 22 is of sufficient diameter to permit cylindrical fastener 4 to pass through and to enter and screw into internal threads inside implant 2. Fastener 4 has a head 22 which, when fastener 4 is screwed completely into threads 16, fits inside notched region 23 atop passage 22, and seats on the flange surface inside region Near the top of projection 11, the circumference around its six sides is sufficiently small to permit projection 11 to initially enter cavity 19 without engaging frictionally the leading edges of the opening to cavity 19. However, as projection 11 enters cavity 19 more fully, the leading edges of each of the sides of the cavity, and then the sides themselves frictionally engage the sides of projection 11 with increasing force. The degree of taper of the sides of projection 11 is sufficiently small to permit projection 11 to enter fully into cavity 19, with the result that surface 18 at the bottom end of abutment 17 seats completely upon surface 10 at the top of implant 2, closing completely the margin between abutment 17 and implant 2.

As FIGS. 5 and 6 show, screwing fastener 4 into threads 16 forces perpendicular walls 20, 21 into anti-rotational, locking engagement with the tapered sidewalls 13 and 14 on male projection 11, thus sealingly seating surface 18 onto surface 10.

FIGS. 3, 4 and 7 show, in exploded detail views, male projection 11 atop implant 2, cavity 19 inside abutment 17, and the resulting anti-rotational, locked structure that results when tapered walls 13, 14 are wedged into cavity 19.

FIGS. 8, 9 and 10 show a second embodiment of a generally cylindrical, endosseous dental implant 100, here with unthreaded external sidewall 101. Sidewall 101 has longitudinal, spaced-apart grooves 102, 103 connected, near the bottom end of implant 100, to round-shaped cross-vents 104, 105 and 106 that form internal opening 107. At the top end of implant 100 is abutment 108 having six-sided, internal cavity 109. Inside cavity 109 are six sidewalls of substantially equal width and length, with each sidewall perpendicular to the longitudinal axis of abutment 108 and with opposing sidewalls parallel to one another.

Inside implant 100 is internally-threaded passage 110 extending downwardly from substantially flat upper surface 111 of abutment 100. Centered at the top end of abutment 100 is six-sided male projection 112 having each of its six sides tapering downwardly and outwardly from upper surface 113 to flat surface 114 that surrounds projection 112 atop implant 100.

Inside abutment 108 is internal passage 115 that receives cylindrical, externally-threaded fastener 116 having head member 117 that seats itself on the surface of notched cavity 118 at the top of abutment 108. When fastener 116 is screwed into the internal threads in passage 110, internal cavity 109 inside abutment 108 is forced onto projection 112 to form an anti-rotational connection and to seal surface 111 on surface 114. At the bottom of implant 100 is apical passage 118 which connects with opening 107.

Figure 12:
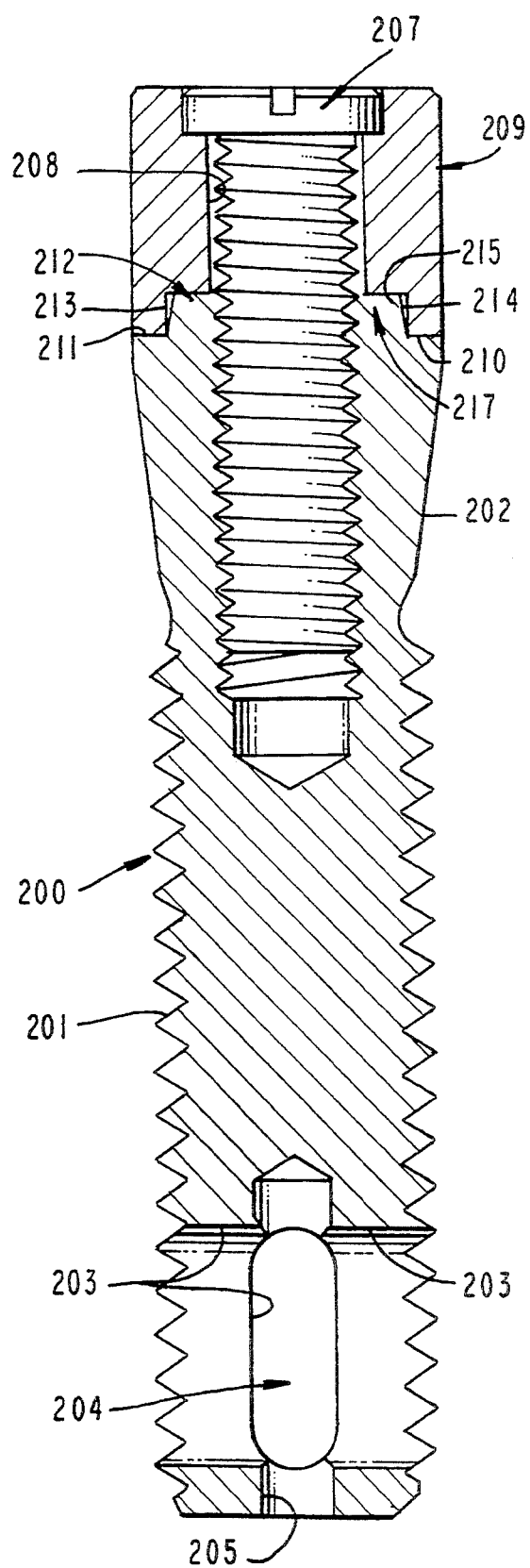

FIGS. 11 and 12 show a third embodiment of a generally cylindrical, endosseous dental implant 200 having externally-threaded sidewalls 201, upwardly and outwardly tapering upper body portion 202 and a plurality of oval-shaped through holes 203 forming an internal passage 204. Apical passage 205 also communicates with internal passage 204. Inside abutment 200 is internally-threaded passage 206, which receives threaded fastener 207. Threaded fastener 207 passes through internal passage 208 in abutment 209 which has substantially the same outer diameter at surface 220 as does abutment 200 at surface 211. Atop implant 211 is male projection 212 with six, downwardly tapering sides 213, 214 and flat upper surface 215. Inside abutment 209 at the bottom is six-sided, internal cavity 217 in which each of the sides is perpendicular to the longitudinal axis of abutment 209 and implant 200. When fastener 207 is screwed completely into internally-threaded 206 and abutment 200, the tapered sidewalls on projection 212 engage, firmly and anti-rotationally, the six internal sides of female cavity 217 in abutment 209.

FIGS. 13 and 14 show a fourth embodiment of a generally cylindrical, endosseous dental implant 300 with an externally-threaded sidewall portion 301, and an upwardly, outwardly tapering upper unthreaded sidewall portion 302. Implant 300 is joined, anti-rotationally, to cavity 315 inside the bottom end of abutment 303 through the tapered sidewalls 304, 305 of male projection 306 atop the flat surface 307 of implant 300. Inside implant 300 is internally-threaded passage 308 that receives threaded fastener 309. Fastener 309 passes through internal passage 310 in abutment 303 before threading into internal passage 308. Abutment 300 includes oval-shaped cross-vents 311, 312 that form internal opening 313. Apical passage 314 leads into opening 313 as well. As in the first, second and third embodiments, the coupling surfaces include the six perpendicular sides inside cavity 315 and the six downwardly-tapered sidewalls 304, 305 of male projection 306 at the top of implant 300.

What is claimed is:

1. An endosseous dental implant adapted for insertion in a passage formed in the jawbone of a patient, said implant having a substantially cylindrical-shaped body, said implant having, at its top end, unthreaded, multi-sided projection means having at least one side that tapers outwardly and downwardly from the upper end of said projection means to the upper surface of said implant, said implant having an internal threaded passage extending through said projection means and downwardly inside the body of the implant from its top end, and an abutment adapted for use with said dental implant, said abutment including an unthreaded, untapered, multi-Sided cavity inside an opening at the bottom end of said abutment, said cavity having the same number of sides as said multi-sided projection means, each of said sides inside said cavity being substantially untapered, said projection means having a size and shape sufficient to fit within, and frictionally engage the sides of said cavity and to pass sufficiently far into said cavity to form a sealing engagement and a locked, anti-rotational connection between the bottom end of said abutment and the top end of said implant, closing the margin between said abutment at the bottom end and said implant at its top end.

2. The implant of claim 1 further comprising fastener means that includes a threaded shaft adapted to pass through an internal passage in said abutment, to screw into said internal threaded passage inside said implant, and to seat said cavity onto said projection means.

3. The implant of claim 1 wherein said abutment comprises a hollow body of a size and shape adapted for use as an abutment, said abutment having, at its bottom end, a substantially flat surface.

4. The implant of claim 1 or claim 2 or claim 3 having, at its top end, a substantially flat surface surrounding said multi-sided projection means, said flat surface having a size and shape adapted to seat firmly and co-extensively upon a corresponding flat surface at the bottom of said abutment when said abutment is seated atop said implant.

5. The implant of claim 1 wherein the tapered sides have sufficient size, shape and degree of taper to substantially prevent rotation of said abutment when said cavity of said abutment is substantially seated on said projection means.

6. The implant of claim 5 further comprising a plurality of threads on the external sidewall surface of said implant.

7. The implant of claim 1 further comprising a plurality of threads on the external sidewall surface of said implant.

8. The implant of claim 1 or claim 2 or claim 3 or claim 5 or claim 6 or claim 7 wherein said projection means has at least two opposing sides that taper outwardly and downwardly from said upper end of said projection means to the upper surface of said implant.

9. The implant of claim 1 or claim 2 or claim 3 or claim 5 or claim 6 or claim 7 wherein said projection means has all of its sides tapering outwardly and downwardly from the upper end of said projection means to the upper surface of said implant.

10. The implant of claim 1 or claim 2 or claim 3 or claim 5 or claim 6 or claim 7 wherein each tapered side of said projection means tapers at an angle in the range of about one degree to about two degrees outwardly and downwardly from the top end of the projection means to the bottom end of the projection means.

11. An endosseous dental implant having a size and shape suitable for insertion in a passage formed in the jawbone of a patient, said implant having a substantially cylindrical-shaped body, said implant having, at its top end, unthreaded, multi-sided projection means having a plurality of sides that taper outwardly and downwardly from the upper end of said projection means to the upper surface of said implant, said projection means being non-rotational with respect to said body of said implant, said implant having an internal threaded passage extending through said projection means and downwardly inside the body of said implant from a point at or below its top end, and an abutment adapted for use with said dental implant, said abutment including an unthreaded, untapered, multi-sided cavity inside an opening at the bottom end of said abutment, said cavity having the same number of sides as said multi-sided projection means, each of said sides inside said cavity being substantially untapered, said projection means having a size and shape sufficient to fit within and frictionally engage the sides of said cavity and to pass sufficiently far into said cavity to form a locked, anti-rotational connection between the bottom end of said abutment and the top end of said implant.

12. The implant of claim 11 further comprising fastener means that includes a threaded shaft adapted to pass through an internal passage in said abutment, to screw into said internal threaded passage inside said implant, and to seat said cavity onto said projection means.

13. The implant of claim 11 further comprising an abutment, said abutment comprising a hollow body of a size and shape adapted for use as an abutment, said abutment having, at its bottom end, a substantially flat surface.

14. The implant of claim 11 or claim 12 or claim 13 having, at its top end, a substantially flat surface surrounding said multi-sided projection means, said flat surface having a size and shape adapted to seat firmly and co-extensively upon a corresponding flat surface at the bottom of said abutment when said abutment is seated atop said implant.

15. The implant of claim 11 wherein the tapered sides have sufficient size, shape and degree of taper to substantially prevent rotation of said abutment when said cavity of said abutment is substantially seated on said projection means.

16. The implant of claim 15 further comprising a plurality of threads on the external sidewall surface of said implant.

17. The implant of claim 11 further comprising a plurality of threads on the external sidewall surface of said implant.

18. The implant of claim 11 or claim 12 or claim 13 or claim 15 or claim 16 or claim 17 wherein said projection means has at least two opposing sides that taper outwardly and downwardly from said upper end of said projection means to the upper surface of said implant.

19. The implant of claim 11 or claim 12 or claim 13 or claim 15 or claim 16 or claim 17 wherein said projection means has all of its sides tapering outwardly and downwardly from the upper end of said projection means to the upper surface of said implant.

20. The implant of claim 11 or claim 12 or claim 13 or claim 15 or claim 16 or claim 17 wherein each tapered side of said projection means tapers at an angle in the range of about one degree to about two degrees outwardly and downwardly from the top end of the projection means to the bottom end of the projection means.

* * * * *